(12) United States Patent
Lai et al.

(10) Patent No.: US 6,355,661 B1
(45) Date of Patent: Mar. 12, 2002

(54) METHODS FOR TREATMENT OF SICKLE CELL ANEMIA

(75) Inventors: Ching-San Lai; Vassil P. Vassilev; Long-Shiuh Chen, all of San Diego, CA (US)

(73) Assignee: Medinox, Inc., San Diego, CA (US)

( * ) Notice: Subject to any disclaimer, the term of this patent is extended or adjusted under 35 U.S.C. 154(b) by 0 days.

(21) Appl. No.: 09/797,649

(22) Filed: Mar. 1, 2001

Related U.S. Application Data

(62) Division of application No. 09/295,153, filed on Apr. 20, 1999, now Pat. No. 6,251,927.

(51) Int. Cl.7 .............................................. A61K 31/425
(52) U.S. Cl. ....................................... 514/365; 514/371
(58) Field of Search .................................. 514/365, 371

(56) References Cited

U.S. PATENT DOCUMENTS

| | | | | |
|---|---|---|---|---|
| 5,599,974 A | * | 2/1997 | Abraham et al. ........... 562/463 |
| 5,631,018 A | * | 5/1997 | Zalipsky et al. ............. 424/264 |
| 5,668,182 A | * | 9/1997 | Abraham et al. ........... 514/699 |
| 5,714,166 A | * | 2/1998 | Tomalia et al. ............. 424/486 |
| 5,723,147 A | * | 3/1998 | Kim et al. ................... 424/450 |
| 5,766,627 A | * | 6/1998 | Sankaram et al. .......... 424/450 |

* cited by examiner

*Primary Examiner*—James H. Reamer
(74) *Attorney, Agent, or Firm*—Stephen E. Reiter; Foley & Lardner

(57) ABSTRACT

The preparation and use of a protected organic aldehyde is described wherein bioavailability of the orally administered therapeutic aldehyde is improved. The protected aldehyde is prepared by reacting the aldehyde with a protecting group, for example, condensing the aldehyde chemically with a thiazolidine-4-carboxylic acid. The improved bioavailability of such orally administered drugs increases the feasibility of delivering sufficient amounts of vanillin or other therapeutic organic aldehydes in vivo to prevent sickling in sickle cell anemia. Combination therapy is also described wherein a protected organic aldehyde is administered to a subject in treatment of sickle cell anemia in conjunction with one or more other drugs, such as pain killers, used in treatment of the symptoms of sickle cell anemia or sickle cell disease.

18 Claims, 1 Drawing Sheet

METHODS FOR TREATMENT OF SICKLE CELL ANEMIA

This application is a divisional of Ser. No. 09/295,153, filed Apr. 20, 1999 now U.S. Pat. No. 6,251,927.

FIELD OF THE INVENTION

The present invention generally relates to methods for treating anemia. More specifically, the present invention relates to methods for treating sickle cell anemia using protected forms(s) of organic aldehydes.

BACKGROUND OF THE INVENTION

Sickle cell disease is a hemolytic disorder, which affects, in its most severe form, approximately 80,000 patients in the United States (see, for example, D. L. Rucknagel, in R. D. Levere, Ed., *Sickle Cell Anemia and Other Hemoglobinopathies*, Academic Press, New York, 1975, p.1). The disease is caused by a single mutation in the hemoglobin molecule; β6 glutamic acid in normal adult hemoglobin A is changed to valine in sickle hemoglobin S. (see, for example, V. M. Ingram in *Nature*, 178:792–794 (1956)). Hemoglobin S has a markedly decreased solubility in the deoxygenated state when compared to that of hemoglobin A. Therefore, upon deoxygenation, hemoglobin S molecules within the erythrocyte tend to aggregate and form helical fibers that cause the red cell to assume a variety of irregular shapes, most commonly in the sickled form. After repeated cycles of oxygenation and deoxygenation, the sickle cell in the circulation becomes rigid and no longer can squeeze through the small capillaries in tissues, resulting in delivery of insufficient oxygen and nutrients to the organ, which eventually leads to local tissue necrosis. The prolonged blockage of microvascular circulation and the subsequent induction of tissue necrosis lead to various symptoms of sickle cell anemia, including painful crises of vaso-occlusion.

Now, most patients with sickle cell disease can be expected to survive into adulthood, but still face a lifetime of crises and complications, including chronic hemolytic anemia, vaso-occlusive crises and pain, and the side effects of therapy. Currently, most common therapeutic interventions include blood transfusions, opioid and hydroxyurea therapies (see, for example, S. K. Ballas in *Cleveland Clin. J. Med.*, 66:48–58 (1999). However, all of these therapies are associated with some undesirable side-effects. For example, repeated blood transfusions are known to be associated with the risks of transmission of infectious disease, iron overload, and allergic and febrile reactions. Complications of opioid therapy may include addiction, seizures, dependency, respiratory depression and constipation.

Hydroxyurea, an inhibitor of ribonucleotide reductase, acts by impairing DNA synthesis in cells (see, for example, J. W., Yarbro in *Semin. Oncol.*, 19:1–10 (1992). For decades, hydroxyurea has been used clinically as an anti-cancer agent for the treatment of leukemia, skin and other cancers. Since early 1980, hydroxyurea has been used to treat patients with sickle cell disease. Sickle cell patients treated with hydroxyurea often seem to have fewer painful crises of vaso-occlusion, fewer hospitalizations and fewer episodes of acute chest syndrome (See, for example, S. Charache et al. in *New Engl. J. Med.*, 332:1317–1322 (1995); S. Charache et al. in *Med.*, 75:300–326 (1996); and J. L. Bauman et al. in *Arch. Intern Med.*, 141:260–261 (1981)). It appears that hydroxyurea treatment increases fetal hemoglobin levels in the red cell, which in turn inhibits the aggregation of sickle cell hemoglobin. However, not all patients in these studies benefited from hydroxyurea treatment, and painful crises of vaso-occlusion were not eliminated in most patients. In fact, a recent clinical trial showed that after a 2-year treatment, fetal hemoglobin levels of patients assigned to the hydroxyurea arm of the study did not differ markedly from their pretreatment levels (see, for example, S. Charache in *Seminars in Hematol.*, 34:15–21 (1997)). Thus, the mechanism of action of hydroxyurea in the treatment of sickle cell anemia remains unclear.

In addition to the limited effectiveness of hydroxyurea therapy, such treatment causes a wide range of undesirable side-effects. The primary side-effect of hydroxyurea is myelosuppression (neutropenia and thrombocytopenia), placing patients at risks for infection and bleeding. In addition, long-term treatment with hydroxyurea may cause a wide spectrum of diseases and conditions, including multiple skin tumors and ulcerations, fever, hepatitis, hyperpigmentation, scaling, partial alopecia, atrophy of the skin and subcutaneous tissues, nail changes and acute interstitial lung disease (see, for example, P. J. M. Best et al. in *Mayo Clin. Proc.*, 73:961–963 (1998); M. S. Kavuru et al. in *Cerebral Arterial Thrombosis*, 87:767–769 (1994); M. J. F. Starmans-Kool et al. in *Ann. Hematol.*, 70:279–280 (1995); and M. Papi et al. in *Am Acad. Dermatol.*, 28:485–486 (1993)).

Since sickle cell disease is a genetic disease, in theory, the gene therapy approach should be considered. In fact, gene therapies employing either ribozyme-mediated or retroviral vector-mediated approaches to replacing the defective human β-globin gene are being actively developed for the treatment of sickle cell disease (see, for example, D. J. Weatherall, *Curr. Biol.*, 8:R696–8 (1998); and R. Pawliuk et al., *Ann. N.Y. Acad. Sci.*, 850:151–162 (1998)). However, the gene therapy approach to treating sickle cell disease involves bone marrow transplantation, a procedure which has its own inherent toxicities and risks (for a review, see, C. A. Hillery in *Curr. Opin. Hematol.*, 5:151–5 (1998)). Thus, there is still a need to develop new and more effective therapeutic agents against sickle cell disease.

The solution behavior of hemoglobin S can be modified chemically, particularly to change its low oxygen affinity and tendency to aggregate upon deoxygenation. Among various covalent modifications, blocking of amino groups of hemoglobin, which can be accomplished under mild conditions, seems to be most favorable and pharmaceutically acceptable. For instance, vanillin (4-hydroxy-3-methoxybenzaldehyde) and other related aromatic aldehydes under physiological conditions are known to bind to the free amino groups of hemoglobin S via the classic Schiff base formation as follows (see, for example, R. H. Zaugg et al. in *J. Biol. Chem.*, 252:8542–8548 (1977)):

Vanillin is a flavorant present in foods and beverages and has been granted GRAS (generally regarded as safe) compound status by the FDA. No toxicity was observed when vanillin was given to rats at high levels for extensive periods (see, for example, E. C. Hagan et al. in *Food Cosmet. Toxicol.*, 5:141 (1967)). For example, no significant differences were observed between test and control rats with respect to body and organ weights, hemotology, and histopathology when rats received vanillin at 1.0% of the diet for 16 weeks, 2.0% and 5.0% for 1 year, or 0.5%, 1.0% and 2.0% for 2 years.

Schiff base formation between hemoglobin S and vanillin produced a marked increase in oxygen affinity and shifts the oxy⇌deoxy equilibrium in favor of the oxy form for hemoglobin S, both in solution and in intact red cells. The locations where vanillin binds to hemoglobin S have also been characterized by X-ray crystallography (see, for example, D. J. Abraham et al. in *Am. J. Heinatol.*, 77:1334–1341 (1991)). Vanillin was shown to bind near His 103α, Cys 104α and Gln 131β, with a secondary binding site located between His 116β and His 117β, a site that has been implicated as a polymer contact residue. Ektacytometric studies also demonstrated that vanillin can inhibit the polymerization process of hemoglobin S under deoxygenated conditions (see, for example, Abraham et al. supra). Together, these studies indicate that vanillin may exhibit two related mechanisms of action as a potential antisickling agent. It not only inhibits sickle polymerization formation, but also shifts the hemoglobin-oxygen association curve to the left, with an increase in the solubility of hemoglobin S molecules. Both mechanisms could lead to the reduction of vaso-occlusion episodes.

Hemoglobin concentration within red cells is about 5 mmoles/liter. Assuming a blood volume of 4 liters in a 60-kg person, about 1 gram of vanillin would be needed in the circulation to exert its anti-sickling effects, taking into account the accumulative increases in the amount of vanillin-HbS adduct. However, orally administered vanillin is poorly bioavailable because of its extensive metabolism in the intestines and liver (see, for example, L. P. Strand and R. R. Scheline in *Xenobiotica*, 5:49–63 (1975)).

Accordingly, there is still a need in the art for new methods for treating sickle cell anemia. In addition, there is a need for combination treatments that utilize compounds useful in treatment of sickle cell anemia in conjunction with other drugs that are useful in treating sickle cell anemia or one or more of the symptoms associated with sickle cell disease.

BRIEF DESCRIPTION OF THE INVENTION

The present invention overcomes many of the problems in the art by providing methods for treatment of sickle cell anemia and methods for combination treatment of sickle cell anemia and one or more of the manifestations of sickle cell disease. The invention is based upon the discovery that certain protected forms of organic aldehydes have utility in treatment of sickle cell anemia, for example, by providing a source of organic aldehyde that forms a Schiff base adduct with hemoglobin S in whole blood.

Accordingly, in accordance with the present invention there are provided methods for treatment of sickle cell anemia in a subject in need thereof comprising administering to the subject an effective amount of a protected organic aldehyde, such as, for example, a thiazolidine having the chemical structure I,

(I)

wherein $R_1$ is —OH, alkoxy, substituted alkoxy, cycloalkoxy, substituted cycloalkoxy, aryloxy, substituted aryloxy, heteroaryloxy, substituted heteroaryloxy, or $N(R_5)_2$ wherein each $R_5$ is independently H, alkyl, substituted alkyl, alkenyl, substituted alkenyl, aryl, substituted aryl, heteroaryl, substituted heteroaryl, and the like, wherein $R_2$ is H or —X—$R_6$ wherein X is carbonyl or sulfonyl and $R_6$ is alkyl, substituted alkyl, aryl, substituted aryl, alkylaryl, or substituted alkylaryl, and the like, and wherein one of $R_3$ and $R_4$ is H and the other is H, alkyl substituted alkyl, cycloalkyl, substituted cycloalkyl, alkenyl, substituted alkenyl, aryl, substituted aryl, heteroaryl, or substituted heteroaryl, and the like.

Particularly useful thiazolidines contemplated for use in practice of the present invention are those wherein $R_3$ and $R_4$ are derived from an arylaldehyde, such as those having the structure II

(II)

wherein each of $R_7$, $R_8$, and $R_9$ are optional and, if present, are independently —OH, alkyl, substituted alkyl, alkoxy, cycloalkoxy, acyloxy, cycloacyloxy, F, Cl, Br, $NO_2$, cyano, or the like.

In accordance with another embodiment of the present invention, there are provided methods for increasing in vivo stability of therapeutic organic aldehyde(s). In the invention in vivo stabilization method, the aldehyde is converted into a protected form thereof, e.g., the aldehyde may be incorporated into a thiazolidine having the chemical structure I above. The oral availability of the organic aldehyde in such invention compounds is increased by from about 4 to about 10 times compared to that of the free organic aldehyde, making them suitable for oral administration. Hence, treatment of sickle cell anemia according to the invention methods affords the considerable advantage that the therapeutic compounds can be administered orally to a subject in need thereof, thereby avoiding the discomfort and inconvenience to the subject of injections.

DETAILED DESCRIPTION OF THE INVENTION

Figure 1:
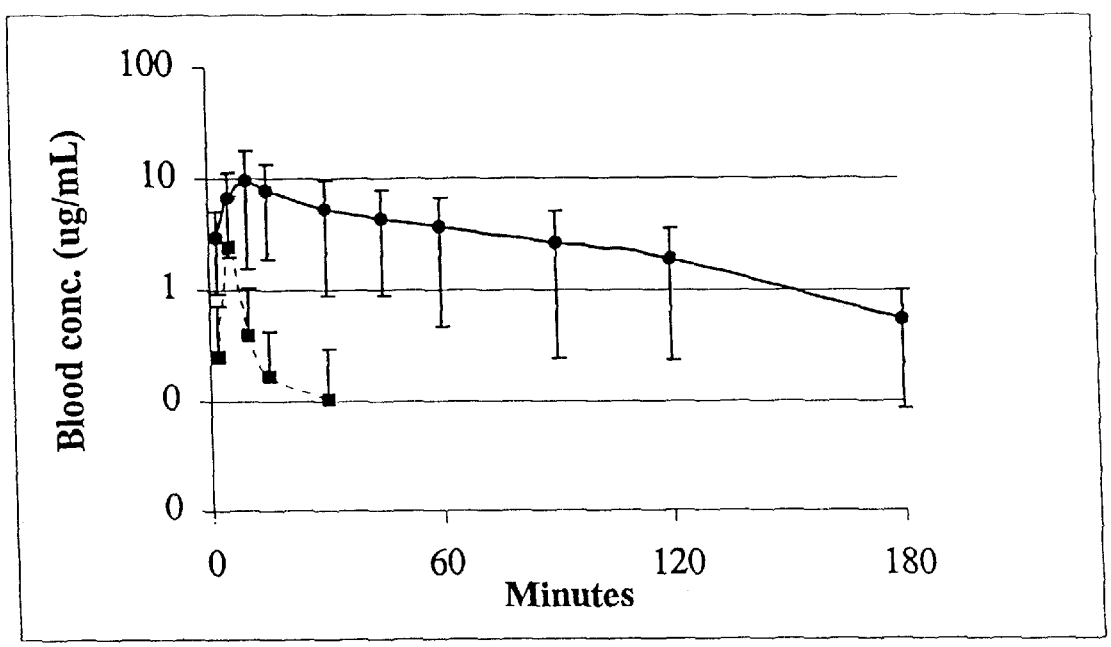
FIG. 1 is a graph showing vanillin blood concentration-time curves after oral administration of vanillin-thiazolidine (closed circles) or vanillin (closed rectangles) in rats.

In accordance with the present invention, there are provided methods for treatment of sickle cell anemia in a subject in need thereof comprising administering to the subject an effective amount of a protected organic aldehyde. As readily recognized by those of skill in the art, organic aldehydes and hydroxy-substituted organic aldehydes can undergo a variety of reactions that render the aldehyde chemically protected. For example, organic aldehydes can be protected by conversion to the corresponding imine, macrocyclic ester/imine, acetal, hemiacetal, macrocyclic ester/hemiacetal, macrocyclic ester/acetal, alcohol, ester, macrocyclic diester, thiazolidine, and the like.

In the embodiment of the invention wherein the protected organic aldehyde is an imine, those of skill in the art recognize that such derivatives can be obtained in a variety of ways, such as, for example, by reaction of an organic aldehyde (R—CHO), optionally hydroxy substituted, with an amine, as follows:

wherein each of R and R' is independently alkyl, substituted alkyl, cycloalkyl, substituted cycloalkyl, aryl, substituted aryl, heteroaryl, substituted heteroaryl, and the like.

In the embodiment of the invention wherein the protected organic aldehyde is a macrocyclic ester/imine, those of skill in the art recognize that such derivatives can be obtained in a variety of ways, such as, for example, by reaction of a hydroxy substituted organic aldehyde with a compound $HOOC-X-NH_2$ wherein X is a suitable bridging species, thereby forming a protected organic aldehyde, as follows:

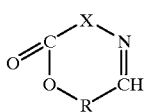

wherein R is as defined above. As readily understood by those of skill in the art, X can vary widely, for example a 4–20 atom bridging species.

In the embodiment of the invention wherein the protected organic aldehyde is an acetal or hemiacetal, those of skill in the art recognize that such derivatives can be prepared in a variety of ways, such as, for example, by reaction of an aldehyde with one or more alcohols as follows

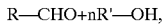

wherein an hemiacetal is formed when n=1 and an acetal is formed when n=2, and wherein R and R' are as defined above.

In the embodiment of the invention wherein the protected organic aldehyde is a macrocyclic ester/hemiacetal, those of skill in the art recognize that such derivatives can be obtained in a variety of ways, such as, for example, by reaction of an hydroxy-substituted organic aldehyde with an hydroxy acid having the structure HOOC—X—CH—OH, wherein X is a suitable bridging species, thereby forming a protected organic aldehyde, as follows:

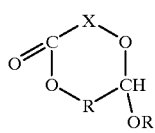

wherein R and X are as defined above.

In the embodiment of the invention wherein the protected organic aldehyde is the corresponding alcohol form, those of skill in the art recognize that such derivatives can be prepared in a variety of ways, such as, for example, by partial reduction of the aldehyde.

In the embodiment of the invention wherein the protected organic aldehyde is a macrocyclic diester, those of skill in the art recognize that such derivatives can be obtained in a variety of ways, such as, for example, by reaction of an hydroxy substituted organic aldehyde with a suitable diacid having the structure, HOOC—X—COOH, wherein X is a suitable bridging species, thereby forming a macrocyclic diester, as follows:

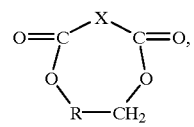

wherein R and X are as defined above.

In the embodiment of the invention wherein the protected organic aldehyde is a cyclic acetal, those of skill in the art recognize that such derivatives can be prepared in a variety of ways, such as, for example, by reaction of an hydroxy substituted organic aldehyde HO—R—CHO, wherein R is as defined above, with a diol having the structure HO—$(CH_2)n$—OH, wherein n is from 2–12, to obtain the cyclic acetal.

In the embodiment of the invention wherein the protected organic aldehyde is a thiazolidine, those of skill in the art realize that such derivatives can be prepared in a variety of ways, such as, for example, by employing the methods disclosed in PCT Application No. EP91/01663, which is incorporated herein by reference in its entirety. Thiazolidines contemplated for use in the practice of the present invention are those having the chemical structure I,

(I)

wherein $R_1$ is —OH, alkoxy, substituted alkoxy, cycloalkoxy, substituted cycloalkoxy, aryloxy, substituted aryloxy, heteroaryloxy, substituted heteroaryloxy, or $N(R_5)_2$ wherein each $R_5$ is independently H, alkyl, substituted alkyl, alkenyl, substituted alkenyl, aryl, substituted aryl, heteroaryl, substituted heteroaryl, and the like, wherein $R_2$ is H or —X—$R_6$, and the like, wherein X is carbonyl or sulfonyl and $R_6$ is alkyl, substituted alkyl, aryl, substituted aryl, alkylaryl, substituted alkylaryl, and the like, and wherein one of $R_3$ and $R_4$ is H and the other is H, alkyl, substituted alkyl, cycloalkyl, substituted cycloalkyl, alkenyl, substituted alkenyl, aryl, substituted aryl, heteroaryl, substituted heteroaryl, and the like.

For example, $R_3$ and $R_4$ can be derived from an aromatic aldehyde such as, for example, vanillin, o-vanillin, isovanillin, gallic aldehyde, and the like. Alternatively, $R_3$ and $R_4$ can be derived from an organic aldehyde, such as 1-hexanal, hexen-2-al, heptanal, 1-octanal, 1-nonanal, decanal (also known as capraldehyde), tetradecanal (also known as myristic aldehyde), undecanal, undecenal, dodecanal (also known as lauryl aldehyde), 2-methyl undecenal, hexyl cinnamaldehyde, amyl cinnamaldehyde, 3,4-dimethoxy benzaldehyde (also known as veratraldehyde), dimethyl heptenal, 2-methyl-3-(p-isopropylphenol)-propionaldehyde (also known as cyclamenaldehyde), 4-iso propyl benzaldehyde (also known as cuminaldehyde), and the like, or suitable combinations of two or more thereof.

It is presently preferred that $R_3$ and $R_4$ are derived from an arylaldehyde, for example an arylaldehyde having formula II:

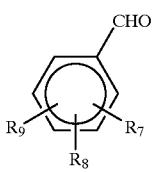

(II)

wherein each of $R_7$, $R_8$, and $R_9$ are optional and, if present, are independently —OH, alkyl, substituted alkyl, alkoxy, cycloalkoxy, acyloxy, cycloacyloxy, F, Cl, Br, $NO_2$, cyano, and the like.

For example, in one presently preferred embodiment, in the arylaldehyde having structure II, $R_7$ is ortho —OH. Alternatively, in structure II both $R_7$ and $R_8$ are —OH, for example with $R_7$ being ortho to the —CHO in structure II and $R_8$ being meta or para to the —CHO. In another embodiment, in structure II $R_7$ is —OH and $R_8$ is —$OCH_3$, for example with $R_7$ being ortho to the —CHO in structure II and $R_8$ being meta or para to the —CHO. In another embodiment, $R_7$, $R_8$ and $R_9$ are all —OH.

As employed herein, "alkyl" refers to alkyl groups having up to about 12 carbon atoms, and "substituted alkyl" refers to alkyl groups bearing one or more substituents selected from carboxyl, —C(O)H, oxyacyl, acyloxy, cycloacyloxy, phenol, phenoxy, pyridinyl, pyrrolidinyl, amino, amido, hydroxy, alkoxy, cycloalkoxy, F, Cl, Br, $NO_2$, cyano, sulfuryl, and the like.

As employed herein "cycloalkyl" refers to cyclic ring-containing groups having in the range of about 3 up to about 8 carbon atoms, and "substituted cycloalkyl" refers to cycloalkyl groups further bearing one or more substituents as set forth above.

As employed herein, "alkenyl" refers to straight or branched chain hydrocarbyl groups having at least one carbon-carbon double bond, and having in the range of about 2 up to about 12 carbon atoms, and "substituted alkenyl" refers to alkenyl groups further bearing one or more substituents as set forth above.

As employed herein, "aryl" refers to aromatic groups having in the range of 6 up to about 14 carbon atoms, and "substituted aryl" refers to aryl groups further bearing one or more substituents as set forth above.

As employed herein, "heteroaryl" refers to aromatic groups containing one or more heteroatoms (e.g., N, O, S, or the like) as part of the ring structure, and having in the range of 5 up to about 13 carbon atoms, and "substituted hetcroaryl" refers to heteroaryl groups further bearing one or more substituents as set forth above.

As employed herein, "alkylaryl" refers to alkyl-substituted aryl groups and "substituted alkylaryl" refers to alkylaryl groups further bearing one or more substituents as set forth above.

As employed herein, "alkoxy" refers to a group —OR, wherein R is an alkyl group as defined above.

As employed herein "cycloalkoxy" refers to a group —OR wherein R is a cycloalkyl as defined above.

As employed herein "acyloxy" refers to a group R—C(O)—O[H] by removal of the hydrogen therefrom, wherein R is an alkyl as defined above.

As employed herein "cycloacyloxy" refers to a group R—C(O)—O[H] by removal of the hydrogen therefrom, wherein R is a cycloalkyl as defined above.

As employed herein, "aryloxy" refers to a group —OAr, wherein Ar is an aryl as defined above, and "substituted aryloxy" refers to aryloxy groups further bearing one or more substituents as set forth above.

As employed herein, "heteroaryloxy" refers to a group —OHt, wherein Ht is a heteroaryl as defined above, and "substituted heteroaryloxy" refers to heteroaryloxy groups further bearing one or more substituents as set forth above.

It is presently preferred in the practice of the present invention that the protected organic aldehyde serve as a source of free or unmodified aldehyde which participates in the formation of a Schiff base adduct with hemoglobin S in whole blood. Compounds that form a Schiff base adduct with hemoglobin S tend to increase the oxygen affinity of erythrocytes, for example by blocking amino groups thereon so as to decrease the sickling of the cells.

In accordance with the present invention, protected organic aldehydes are administered to the blood stream, for example, parenterally, orally, intraarticularly, intravenously, intramuscularly, intraperitoneally, intradermally, intratracheally, and the like, as well as by a combination of any two or more thereof.

Optionally, the invention therapeutic methods can further comprise administration to the subject of a drug useful in treatment of sickle cell anemia or the symptoms and/or conditions known as sickle cell disease, in addition to the protected organic aldehyde(s) described hereinabove. For example, the invention method can further comprise administering to the subject, in addition to the protected organic aldehyde(s) described hereinabove, one or more compounds useful in treatment of the acute pain, inflammation, and depression associated with clogging of blood vessels, and the like. Therefore in one embodiment, the invention method further comprises administration to the subject of an effective amount of one or more drug effective against pain. Examples of drugs useful for this purpose include nonopioid analgesics (such as acetaminophen, and the like), nonsteroidal anti-inflammatories (such as ibuprofen, naproxen ketorolac, and the like), acetylsalicylic acid (aspirin), non-acetylated salicylates (such as diflunisal, choline magnesium trisalicylate, and the like). Opioid analgesics, such as the weak opioid agonists codeine, oxycodone, dihydrocodeine, hydrocodone, and the like, or strong opioid agonists, such as morphine, hydromorphone, meperidine, oxymorphone, levorphanol, fentanyl and methadone, and the like, may also be used.

Additional drugs useful in the treatment of symptoms of sickle cell disease or the side effects of drug therapy may also be coadministered with the invention protected organic aldehyde(s), such as, for example, hydroxyurea, erythropoietin, riboflavin, iron chelators, (e.g., deferoxamine, deferiprone, or dithiocarbamate), isobutyramide, zinc therapy, piracetam, etilefrine, L-glutamine therapy, N-acetylcysteine, cromolyn sodium, arginine butyrate, clotrimazole, an antihistamine, an antidepressant, a benzodiazepine, a phenothiazine, an antiemetic, a laxative, and the like, as well as combinations of any two or more thereof. One or more blood transfusions can also be coadministered with the invention protected organic aldehyde(s) in the treatment of sickle cell anemia.

As used herein the term "sickle cell disease" refers to a variety of clinical problems attendant upon sickle cell anemia, especially in those subjects who are homozygotes for the sickle cell substitution in Hb S. Among the constitutional manifestations referred to herein by use of the term of sickle cell disease are delay of growth and development, an increased tendency to develop serious infections, particularly due to pneumococcus, marked impairment of splenic function, preventing effective clearance of circulating bacteria, with recurrent infarcts and eventual destruction of splenic tissue. Also included in the term "sickle cell disease" are acute episodes of musculoskeletal pain, which affect primarily the lumbar spine, abdomen, and femoral shaft, and which are similar in mechanism and in severity to the bends. In adults, such attacks commonly manifest as mild or moderate bouts of short duration every few weeks or months interspersed with agonizing attacks lasting 5 to 7 days that strike on average about once a year. Among events known to trigger such crises are acidosis, hypoxia and dehydration, all of which potentiate intracellular polymerization of HbS (J. H. Jandl, *Blood: Textbook of Hematology*, 2nd Ed., Little, Brown and Company, Boston, 1996, pages 544–545).

In accordance with another embodiment of the present invention, the therapeutic method can further comprise administering to the subject, in addition to the invention protected organic aldehyde(s), one or more compounds known in the art to be useful in conventional treatments of anemia, such as hydroxyurea, erythropoietin, riboflavin, an iron chelator, isobutyramide, zinc, piracetam, etilefrine, L-glutamine, cromolyn sodium, or N-acetylcysteine, and the like.

In accordance with yet another embodiment of the present invention, the therapeutic method further comprises administration to the subject of a blood transfusion.

In accordance with the invention methods, the drug other than the protected organic aldehyde(s) and/or the blood transfusion can be administered concurrently with the protected organic aldehyde(s), or before, or after administration of the protected organic aldehyde(s), at the discretion of the medical practitioner.

The protected organic aldehyde(s) and, optionally, the drug other than a protected organic aldehyde(s) used in the invention methods is each administered in an "effective amount." An effective amount is the quantity of a protected organic aldehyde(s) or drug other than a protected organic aldehyde(s) according to the invention method necessary to prevent, to cure, or at least partially arrest, a symptom of sickle cell anemia in a subject or of a disease state associated therewith (i.e., sickle cell disease). A subject is any mammal, preferably a human. Amounts effective for therapeutic use will, of course, depend on the severity of the anemia and the weight and general state of the subject, as well as the route of administration. Since individual subjects may present a wide variation in severity of symptoms and each protected organic aldehyde may have its unique therapeutic characteristics, it is up to the practitioner to determine a subject's response to treatment and to vary the dosages accordingly.

Dosages used in vitro may provide useful guidance with respect to the amounts of the pharmaceutical composition useful for in vivo administration, and animal models may in some cases be used to determine effective dosages for treatment of particular disorders. In general, however, it is contemplated that an effective amount of the protected organic aldehyde(s) will be an amount within the range from about 10 µg up to about 100 mg per kg body weight. Various considerations in arriving at an effective amount are described, e.g., in *Goodman And Gilman's: The Pharmacological Bases of Therapeutics*, 8th ed., Pergamon Press, 1990; and *Remington's Pharmaceutical Sciences*, 17th ed., Mack Publishing Co., Easton, Pa., 1990.

In one embodiment of the invention method, the protected organic aldehyde(s) according to the invention are administered in a slow release delivery vehicle, for example, encapsulated in a colloidal dispersion system or in polymer stabilized crystals. Useful colloidal dispersion systems include nanocapsules, microspheres, beads, and lipid-based systems, including oil-in-water emulsions, micelles, mixed micelles, and liposomes. The colloidal system presently preferred is a liposome or microsphere. Liposomes are artificial membrane vesicles which are useful as slow release delivery vehicles when injected or implanted. Some examples of lipid-polymer conjugates and liposomes are disclosed in U.S. Pat. No. , 5,631,018, which is incorporated herein by reference in its entirety. Other examples of slow release delivery vehicles are biodegradable hydrogel matrices (U.S. Pat. No. 5,041,292), dendritic polymer conjugates (U.S. Pat. No. 5,714,166), and multivesicular liposomes (Depofoam®, Depotech, San Diego, Calif.) (U.S. Pat. Nos. 5,723,147 and 5,766,627).

The protected organic aldehyde(s) can be administered according to the invention method in a pharmaceutically acceptable carrier comprising one or more adjuvants which facilitate delivery, such as inert carriers, or colloidal dispersion systems. Representative and non-limiting examples of such inert carriers can be selected from water, isopropyl alcohol, gaseous fluorocarbons, ethyl alcohol, polyvinyl pyrrolidone, propylene glycol, a gel-producing material, stearyl alcohol, stearic acid, spermaceti, sorbitan monooleate, methylcellulose, and the like, as well as suitable combinations of any two or more thereof.

The protected organic aldehyde(s) used in the invention methods can also be formulated as a sterile injectable suspension according to known methods using suitable dispersing or wetting agents and suspending agents. The sterile injectable preparation may also be a sterile injectable solution or suspension in a non-toxic parenterally-acceptable diluent or solvent, for example, as a solution in 1,4-butanediol. Sterile, fixed oils are conventionally employed as a solvent or suspending medium. For this purpose any bland fixed oil may be employed, including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate, or the like. Buffers, preservatives, antioxidants, and the like, can be incorporated as required, or, alternatively, can comprise the formulation.

The protected organic aldehyde(s) contemplated for use in the invention methods herein are preferably formulated for oral administration, for example, as tablets, troches, lozenges, aqueous or oily suspensions, dispersible powders or granules, emulsions, hard or soft capsules, or syrups or elixirs. Fonnulations intended for oral use may be prepared according to any method known in the art for the manufacture of pharmaceutical formulations. In addition, such formulations may contain one or more agents selected from a sweetening agent (such as sucrose, lactose, or saccharin), flavoring agents (such as peppermint, oil of wintergreen or cherry), coloring agents and preserving agents, and the like, in order to provide pharmaceutically elegant and palatable preparations. Tablets containing the active ingredients in admixture with non-toxic pharmaceutically acceptable excipients may also be manufactured by known methods. The excipients used may be, for example, (1) inert diluents such as calcium carbonate, lactose, calcium phosphate, sodium phosphate, and the like; (2) granulating and disintegrating agents such as corn starch, potato starch, alginic acid, and the like; (3) binding agents such as gum tragacanth, corn starch, gelatin, acacia, and the like; and (4) lubricating agents such as magnesium stearate, stearic acid, talc, and the like. The tablets may be uncoated or they may be coated by known techniques to delay disintegration and absorption in the gastrointestinal tract, thereby providing sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874, to fonn osmotic therapeutic tablets for controlled release.

In some cases, formulations for oral use may be in the form of hard gelatin capsules wherein the protected organic aldehyde(s) as described herein are mixed with an inert solid diluent, for example, calcium carbonate, calcium phosphate, kaolin, or the like. They may also be in the form of soft gelatin capsules wherein the protected organic aldelhyde(s) are mixed with water or an oil medium, for example, peanut oil, liquid paraffin, or olive oil.

The term "unit dose," when used in reference to a protected organic aldehyde herein, refers to a quantity thereof suitable as unitary dosage for the subject, each unit containing a predetermined quantity of active material calculated to produce the desired therapeutic effect in association with the required pharmaceutically acceptable carrier and/or vehicle therefor. Generally the unit dose of a particular protected organic aldehyde is determined with respect to the level of anemia whose effects are sought to be counteracted at the appropriate time. For example, in humans, the invention protected organic aldehyde(s) is administered orally at a dose of from about 10 μg to about 100 mg/kg. It is presently preferred that the protected organic aldehyde(s) be formulated for oral administration.

In accordance with another embodiment of the invention methods, the invention protected organic aldehyde(s) are administered in a time release delivery vehicle that releases the protected organic aldehyde(s), and optional drugs other than a protected organic aldehyde encapsulated therein, over an extended period of time to a subject in need thereof. In one embodiment, the time release delivery vehicle is selected to release the protected organic aldehyde(s) over a period of from 30 minutes to several days.

The methods of the invention are particularly suited to reducing the symptoms of sickle cell anemia in subjects who are homozygotes for the substitution of valine for glutamic acid at the sixth residue of the β chain of the hemoglobin molecule known as hemoglobin S. The protected organic aldehyde(s) acts as a pro-drug of vanillin and other therapeutic aldehydes wherein bioavailability of the orally administered therapeutic aldehyde is improved. With the improvement in bioavailability, it is now more feasible to deliver sufficient amounts of vanillin and other therapeutic aldehydes in vivo to prevent sickling in sickle cell anemia.

In another embodiment, the invention provides a kit comprising a unit dose of an invention protected organic aldehyde(s) in a pharmaceutically acceptable carrier, optionally contained within a time release vehicle. The rate of release of the protected organic aldehyde(s) from the time release vehicle is generally in the range from about 0.01 mmoles/kg body weight of the subject/hour up to about 1.0 mmoles/kg/hr.

Depending on the mode of delivery employed, the invention protected organic aldehyde(s) can be administered in a variety of pharmaceutically acceptable forms, such as in the form of a solid, solution, emulsion, dispersion, micelle, liposome, and the like, wherein the protected organic aldehyde(s) are in admixture with an organic or inorganic carrier or excipient suitable for enteral or parenteral applications. The active ingredients may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. The active compounds are included in the pharmaceutical formulation in an amount sufficient to produce the desired effect upon the symptoms of sickle cell anemia.

The invention will now be described in greater detail by reference to the following non-limiting examples.

EXAMPLE 1

Synthesis of Ethyl 2-(4-hydroxy-3-methoxyphenyl)-1,3-thiazolidine-4-carboxylate (1)

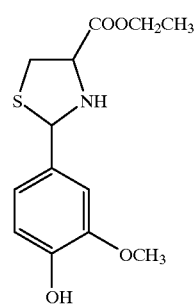

1

To a solution of 1.52 g (10 mM) of vanillin (4-hydroxy-3-methoxybenzaldehyde) in 20 mL of absolute ethanol was added a solution of 1.85 g (10 mM) L-cysteine ethyl ester hydrochloride in 15 mL absolute ethanol, containing 1.7 mL (10 mM) of N-ethyldiisopropylamine. The reaction mixture was stirred at room temperature for about six hrs, until no starting material was present when monitored by thin layer chromatography (TLC). After adding 200 mL of water with stirring, the white precipitate was filtered, washed with 2×50 mL water, and vacuum dried. Yield 1.9 g (67%) of 1. $^1$H NMR (DMSO-$d_6$; ~1:1 diastereoisomeric mixture at C2)δ (1.22 m, 3H); (3.01 m and 3.15 m, 1H); (3.33 m, 2H); (3.75 s and 3.77 s, 3H); (4.15 m, and 4.38 bs, 2H); (5.40 d and 5.49 d, 1H); 6.79–6.73 m, 2H); 6.83–6.89 m 1H); (7.02 d and 7.12d, 1H); (8.99 s and 9.05 s, 1H). Mass analysis: Calculated for $C_{13}H_{17}NO_4S$:284 [M+H]$^+$. Found: 284.

EXAMPLE 2

Synthesis of Ethyl 2-(3,4,5-trihydroxyphenyl)-1,3-thiazolidine-4-carboxylate (2)

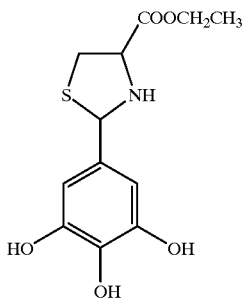

2

To a solution of 1.91 g (11 mM) of gallic aldehyde monohydrate (3,4,5-trihydroxybenzaldehyde) in 20 mL of absolute ethanol is added a solution of 2.06 g (11 mM) L-cysteine ethyl ester hydrochloride in 20 mL absolute ethanol, containing 1.88 mL (11 mM) of N-ethyldiisopropylamine. The reaction mixture is stirred at room temperature for about three hrs, until no starting material is present when monitored by TLC. Concentration under vacuum by rotary evaporator produced an yellow oil, which is purified by flash chromatography on silica gel (hexane:ethylacetate ~7:3). Evaporation of the solvents and drying under high vacuum gave an yellow-orange amorphous product 2. Yield 2.5 g (81%). $^1$H NMR (DMSO-$d_6$; ~1:1 diastereoisomeric mixture at C2) δ ; (1.22 m, 3H); (3.00 m and 3.11 m, 1H); (3.25–3.52 m, 2H); (3.88 m and 4.30 m, 1H); (4.14 m 2H); (5.26 and 5.39 each d, 1H); (6.37 s, 1H); (6.42 s, 1H); (8.10 brd, 1H); (8.85 brd, 2H). Mass analysis: Calculated for $C_{12}H_{15}NO_5S$:284 [M–H]$^-$. Found: 284.

EXAMPLE 3

Synthesis of 3-acetyl-2-(2,5-dihydroxyphenyl)-1,3-thiazolidine-4-carboxylic acid (3)

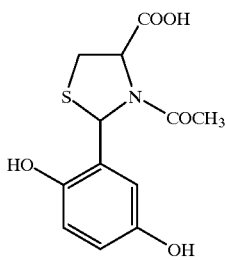

3

To a solution of 1.16 g (4.8 mmol) of 2-(2,5-dihydroxyphenyl)-1,3-thiazolidine-4-carboxylic acid (1:1 mixture of isomers at C2) in 10 mL dimethylformamide (DMF) was added 0.388 mL of pyridine (4.8 mmol), and the solution was cooled to –30° C. with a dry ice acetone bath. Under nitrogen atmosphere, 0.341 mL (4.8 mmol) of acetyl chloride was added to the heterogeneous mixture with constant stirring. The cooling bath was removed and the reaction mixture was allowed to warm up gradually to room temperature. After stirring for an additional 3.5 hrs, 85 mL of water and 0.87 mL 37% HCl were added to the solution, and the solution was allowed to stand at +4° C. overnight. The precipitate was filtered and washed with 5 mL of water. After drying at high vacuum, 0.59 g of N-acetylated product (3a) was obtained, which turned out to be one pure diastereoisomer. $^1$H NMR (CD$_3$OD, mixture of rotamers ~3:1)δ; (1.92 s and 2.15 s, 3H), (3.2 d, J=12.8 Hz and 3.40 d, J=12.1 Hz, 1H), (3.50 dd, J=12.5 and 12.5 Hz, 1H), (5.19 d, J=7.1 Hz and 5.26 d, J=6.06 Hz, 1H), (6.33 s and 6.36 s, 1H), (6.44 d, J=2.9 Hz and 6.42 d, J=2.9 Hz, 1H), (6.58 dd, J=2.6 and 8.7 Hz, 1H), (6.66 d, J=8.4 Hz and 6.52 d, J2.9 Hz, 1H).

After exhaustively extracting the filtrate with ethyl acetate (10×25 mL), washing the organic extract with water, drying with MgSO$_4$, and evaporating of the solvent, 0.59 g of the other isomer (3b) was produced as an yellow oil. Total yield 80%. After dissolving the oil in less than 1 mL ethyl acetate, a crystalline precipitate was obtained. The second isomer cocrystallized with dimethylformamide in a ratio 3b: DMF= 1:1. $^1$H NMR (DMSO-$d_6$, mixture of rotamers ~4:1)δ; 1.79 s and 2.06 s, 1H; 3.02 dd, J=9 Hz, 11.7 Hz, 1H; 3.35 m, 2H; 4.58 dd, J=6.4 Hz, 8.6 Hz and 5.06 t, J=5.7 Hz; 6.24 s and 6.26 s, 1H; 6.44 dd, J=2.7 Hz, 8.6 Hz and 6.61 d, J=8.6 Hz, 1H; 6.53 dd, J=2.8 Hz, 8.3 Hz, 1H; 7.01 d, J=2.4 Hz and 7.34 d, J=2.8 Hz, 1H; 8.54 s and 38.71 s, 1H; 8.90 s and 9.16s, 1H.

EXAMPLE 4

Synthesis of 3-acetyl-2-(2-hydroxy-5-acetyloxyphenyl)-1,3-thiazolidine-4-carboxylic acid (4) or 3-acetyl-2-(2-acetyloxy-5-hydroxyphenyl)-1,3-thiazolidine-4-carboxylic acid (4') (The assignment of 5-acetyl vs. 2-hydroxy is tentative.)

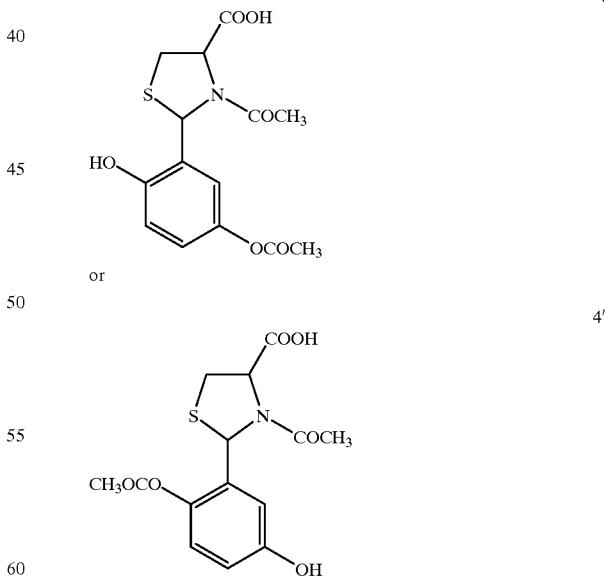

To a solution of—1.42 g (5 mmol) of 3-acetyl-2-(2,5-dihydroxyphenyl)-1,3-thiazolidine-4-carboxylic acid (3a) in 15 mL dimethylformamide was added 0.890 mL of pyridine (11 mmol) and the solution was cooled to –30° C. with a dry ice acetone bath. Under nitrogen atmosphere, 0.782 mL of acetyl chloride (15 mmol) was added to the heterogenous mixture under constant stirring. The cooling bath was removed and the reaction mixture was allowed to warm up gradually to room temperature. After stirring for additional 1 hr, the reaction mixture was evaporated under high vacuum at room temperature. To the oily, viscous syrup was added 15 mL of water and 1.5 mL of concentrated HCl. After sonication for about a minute, the precipitate was formed and allowed to stand at +4° C. for half an hour. The product was filtered and washed with 3×20 mL of water. After drying at high vacuum, 0.45 g of acetylated product (4 or 4') was obtained (24%). An additional amount (0.14 g, 8%) of product was obtained from the filtrate after 16 hrs at room temperature. $^1$H NMR (DMSO-$d_6$; ~1:1 diastereoisomeric mixture at C2)δ; 1.76 s and 2.02 s, 3H; 2.20s and 2.21 s, 3H; 3.14 d, J=12.6 Hz and 3.28 m, 3H; 5.09 d, J=7 Hz and 5.32 d, J=5.8 Hz, 1H; 6.17 s and 6.21 s, 1H; 6.72–6.88 m, 3H, 9.79 s and 10.03 s, 1H.

EXAMPLE 5

Synthesis of 3-acetyl-2-(2,5-diacetyloxyphenyl)-1,3-thiazolidine-4-carboxylic acid (5)

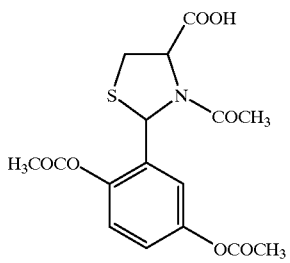

To a solution of 0.241 g (0.85 mmol) of 2-(2,5-dihydroxyphenyl)-1,3-thiazolidine-4-carboxylic acid (1:1 mixture of isomers at C2) was added 3 mL of pyridine, and the solution was cooled to −30° C. with a dry ice acetone bath. To the heterogeneous mixture was added 0.34 mL of acetyl chloride under constant stirring. The cooling bath was removed and the reaction mixture was allowed to warm up gradually to room temperature. After overnight stirring at room temperature, the solvent was removed under high vacuum. To the remaining oily residue were added 19 mL of water and 1 mL concentrated HCl. The precipitate was filtered and washed with 2×5 mL of water. After drying at high vacuum, 0.13 g of acetylated product (5) was obtained (34%), as a mixture of diastereoisomers and rotamers. $^1$H NMR (DMSO-$d_6$) 67 ; 1.76 s, 1.79 s, 1.99 s, 2.03 s, 2.06 s, 2.26 s, 2.33 s, 2.34 s, 9H; 3.2–3.4 m, 3H; 5.11 d, J=8 Hz and 5.36 d, J=8 Hz, 1H; 6.10 s, 6.20 s, 6.33 s and 6.36 s 1H; 6.99–7.22 m, 2H; 12.95 bs, 1H.

EXAMPLE 6

Synthesis of Methyl 2-(2,5-dihydroxyphenyl)-1,3-thiazolidine-4-carboxylate (6)

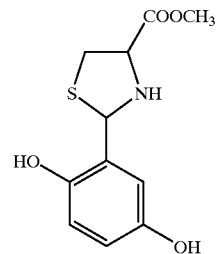

The procedure described below for preparation of ethyl-(2,5-dihydroxyphenyl)-1,3-thiazolidine-4-carboxylate (7) was employed to make 6, except the methyl ester of L-cysteine hydrochloride was employed as starting material.

EXAMPLE 7

Synthesis of Ethyl 2-(2,5-dihydroxyphenyl)-1,3-thiazolidine-4-carboxylate (7)

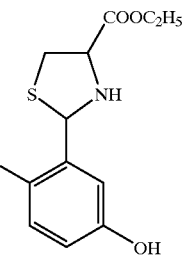

To a round bottom flask, equipped with magnetic stirrer, containing 9.25 g (50 mM) ethyl ester of L-cysteine hydrochloride in 75 mL of absolute ethanol was added 8.4 mL (48 mM) ethyldulsopropylamine. A clear solution was obtained after stirring for several minutes with a magnetic stirrer under nitrogen. To this solution was added 6.65 g (49 mM) 2,5-dihydroxybenzaldehyde in 50 mL absolute ethanol, and the reaction mixture was stirred for another 4 hrs. Evaporation to dryness produced a viscous oil, which was dissolved in 20 mL absolute ethanol and loaded on a silica gel column. Elution with ethylacetate/hexane (at molar ratios from 2:8 to 3.5:6.5) produced 5.9 g of the desired product. $^1$H NMR (DMSO-$d_6$; 1:1 diastereoisomeric mixture at C2)δ; 1.21–1.25 m 3H; 2.95–3.02 m and 3.19–3.22 m, 2H; (3.5 m, 3.76 m 3.90 m and 4.25 m, 2H); 4.15 m, 2H; (5.56 d, J=11.9 Hz and 5.75 d, J=9.9 Hz, 1H); (6.45–6.48 dd, J=2.9 Hz, 8.7 Hz, 6.52–6.55 dd, J=2.9 Hz, 8.7 Hz, 6.57 d, J=8.8 Hz, 6.61 d, J=8.8 Hz 2H); 6.76 dd, J=2.8 Hz, 9.2 Hz, 1H; 8.64 s and 8.75 s, 1H; 9.01 s and 9.19 s 1H.

EXAMPLE 8

Synthesis of Methyl-3-acetyl-2-(2,5-dihydroxyphenyl)-1,3-thiazolidine-4-carboxylate (8)

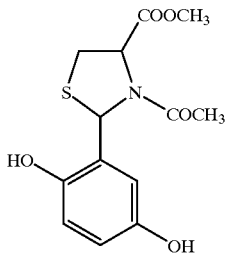

The procedure described above for preparation of 3-acetyl-2-(2,5-dihydroxyphenyl)-1,3-thiazolidine-4-carboxylic acid (3) was followed to prepare 8, except that the methyl ester of the thiazolidine starting material was employed.

EXAMPLE 9

Synthesis of Methyl-3-acetyl-2-(2-hydroxy-5-acetyloxyphenyl)-1,3-thiazolidine-4-carboxylate (9)

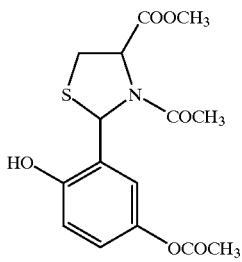

The procedure described above for preparation of 3-acetyl-2-(2-hydroxy-5-acetyloxyphenyl)-1,3-thiazolidine-4-carboxylic acid (4) was followed to prepare 9, except that a 2,5-diacetyloxy thiazolidine starting material was employed.

EXAMPLE 10

Synthesis of Methyl-3-acetyl-2-(2,5-diacetyloxyphenyl)-1,3-thiazolidine-4-carboxylate (10)

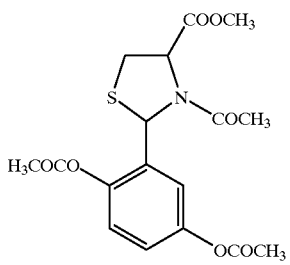

The procedure described above for preparation of 3-acetyl-2-(2,5-diacetyloxyphenyl)-1,3-thiazolidine-4-carboxylic acid (5) was followed to prepare 10, except that a 2,5-dimethyl ester of L-cysteine hydrochloride was employed as starting material.

EXAMPLE 11

Synthesis of Ethyl-3-acetyl-2-(2,5-dihydroxyphenyl)-1,3-thiazolidine-4-carboxylate (11)

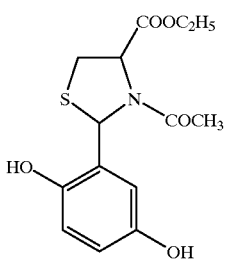

The procedure described above for preparation of 3-acetyl-2-(2,5-dihydroxyphenyl)-1,3-thiazolidine-4-carboxylic acid (3) was followed for preparation of 11, except that an ethyl ester of L-cysteine hydrochloride was employed as starting material.

EXAMPLE 12

Synthesis of Ethyl-3-acetyl-2-(2-hydroxy-5-acetyloxyphenyl)-1,3-thiazolidine-4-carboxylate (12)

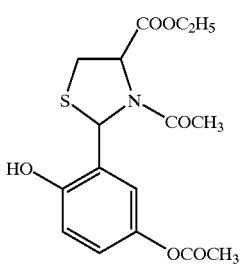

The procedure described above for the preparation of 3-acetyl-2-(2-hydroxy-5-acetyloxyphenyl)-1,3-thiazolidine- 4-carboxylic acid (4) was followed to prepare 12, except an ethyl ester of the thiazolidine was employed as starting material.

EXAMPLE 13

Synthesis of Ethyl-3-acetyl-2-(2,5-diacetyloxyphenyl)-1,3-thiazolidine-4-carboxylate (13)

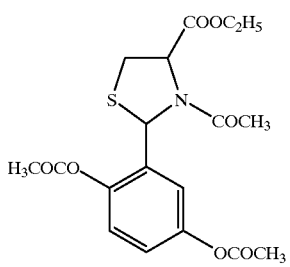

13

The procedure described above for preparation of 3-acetyl-2-(2,5-diacetyloxyphenyl)-1,3-thiazolidine-4-carboxylic acid (5) was followed to obtain 13, except an ethyl ester of the thiazolidine was employed as starting material.

EXAMPLE 14

Synthesis of 2-(2,5-dihydroxyphenyl)-1,3-thiazolidine-N-(5-methyl-2-thiazolyl)-4-carboxamide (14)

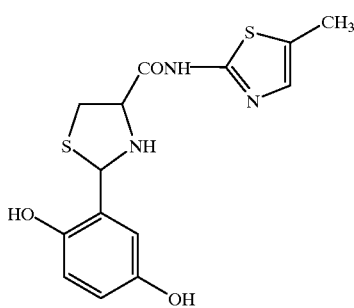

14

The procedure employed here is similar to the procedure described above for the preparation of 3-acetyl-2-(2,5-diacetyloxyphenyl)-1,3-thiazolidine-4-carboxylic acid (5), but requires protection of the NH group of 2-(2,5-dihydroxyphenyl)-1,3-thiazolidine-4-carboxylic acid before coupling with the amine.

EXAMPLE 15

Synthesis of 3-acetyl-2-(2,5-dihydroxyphenyl)-1,3-thiazolidine-N-(5-methyl-2-thiazolyl)-4-carboxamide (15)

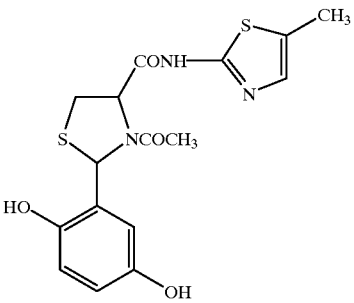

15

To a solution 0.71 g (2.5 mmol) 3-acetyl-2-(2,5-dihydroxyphenyl)-1,3-thiazolidine-4-carboxylic acid (3a) in 5 mL DMF was added 0.203 mL (2.5 mmol) of pyridine, and the mixture was cooled to −10° C. To the reaction mixture was added 0.138 mL thionyl chloride with constant stirring and the cooling bath was removed. The reaction mixture was stirred at room temperature for 4 hrs and then a solution of 0.285 g (2.5 mmol) 2-amino-5-methylthiazole in 2 mL DMF and 0.203 mL pyridine was added dropwise. The stirring continued for another 3 hrs. Evaporation of the solvent and recrystallization from ethanol/water produced 0.6 g, (63%) of the desired product. $^1$H NMR was in good agreement for the desired structure and showed complex broadened signals due to the existence of rotamers (two amide bonds) in addition to the diastereoisomeric mixture. Mass: Calculated for $C_{16}H_{17}N_3O_4S_2$: 379. Found: 380 $[M+H]^+$.

EXAMPLE 16

Synthesis of 3-acetyl-2-(2-hydroxy-5-acetyloxyphenyl)-1,3-thiazolidine-N-(5-methyl-2-thiazolyl)-4-carboxamide (16)

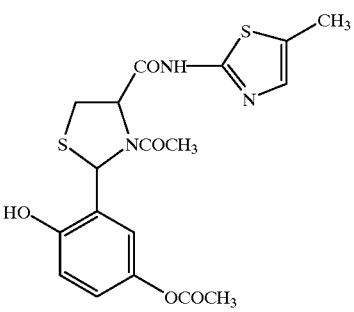

16

The procedure described above for the preparation of 3-acetyl-2-(2,5-dihydroxyphenyl)- 1,3-thiazolidine-N-(5-methyl-2-thiazolyl)-4-carboxamide (15) was followed, except that 3-acetyl-2-hydroxy-5-acetyoxyphenyl)-1,3-thiazolidine-4-carboxylic acid was substituted for 3-acetyl-2-(2,5-dihydroxyphenol)-1,3-thiazolidine-4-carboxylic acid.

EXAMPLE 17

Synthesis of 3-acetyl-2-(2,5-diacetyloxyphenyl)-1,3-thiazolidine-N-(5-methyl-2-thiazolyl)-4-carboxamide (17)

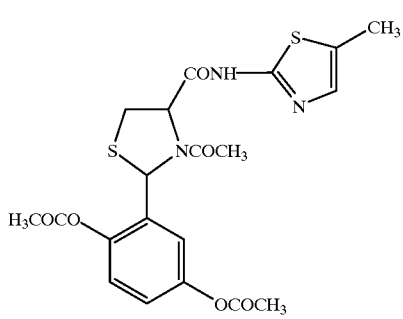

The procedure described above for preparation of 3-acetyl-2-(2,5-dihydroxyphenyl)-1,3-thiazolidine-N-(5-methyl-2-thiazolyl)-4-carboxamide (15) was repeated, except that 3-acetyl-2-(2,5-diacetyloxyphenyl)-1,3-thiazolidine-4-carboxylic acid is substituted for 3-acetyl-2-(2,5-dihydroxyphenyl)-1,3-thiazolidine-4-carboxylic acid.

EXAMPLE 18

Synthesis of 2-(2,5-dihydroxyphenyl)-1,3-thiazolidine-N-2-pyridinyl-4-carboxamide (18)

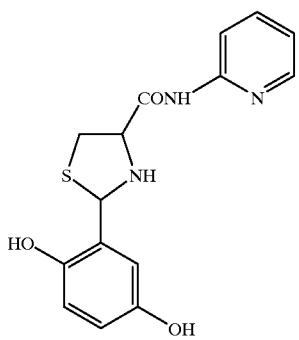

The procedure described above for preparation of 3-acetyl-2-(2,5-dihydroxyphenyl)-1,3-thiazolidine-N-(5-methyl-2-thiazolyl)-4-carboxamide (15) was employed for preparation of 18, except that the thiazolidine starting material lacked the 3-acetyl substituent and pyridine was used as a starting material.

EXAMPLE 19

Synthesis of 3-acetyl-2-(2,5-dihydroxyphenyl)-1,3-thiazolidine-N-2-pyridinyl-4-carboxamide (19)

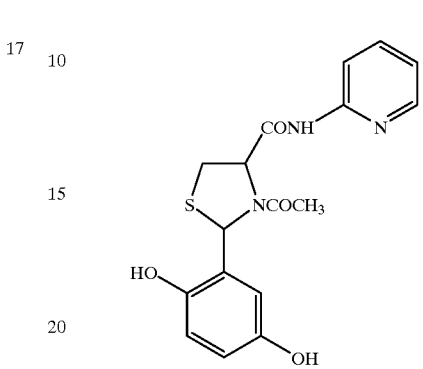

The procedure described above for preparation of 3-acetyl-2-(2,5-dihydroxyphenyl)-1,3-thiazolidine-N-(5-methyl-2-thiazolyl)-4-carboxamide (15) was employed for preparation of 19, except that pyridine was used as a starting material.

EXAMPLE 20

Synthesis of 3-acetyl-2-(2-hydroxy-5-acetyloxyphenyl)-1,3-thiazolidine-N-2-pyridinyl-4-carboxamide (20)

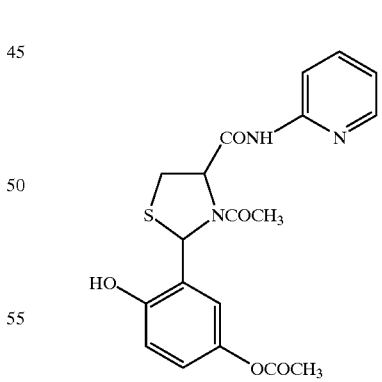

The procedure described above for preparation of 3-acetyl-2-(2,5-dihydroxyphenyl)-1,3-thiazolidine-N-(5-methyl-2-thiazolyl)-4-carboxamide (15) was followed for the preparation of 20, except that pyridine and a methyl ester of the thiazolidine starting material were employed.

EXAMPLE 21

Synthesis of 3-acetyl-2-(2,5-diacetyloxyphenyl)-1,3-thiazolidine- N-2-pyridinyl-4-carboxamide (21)

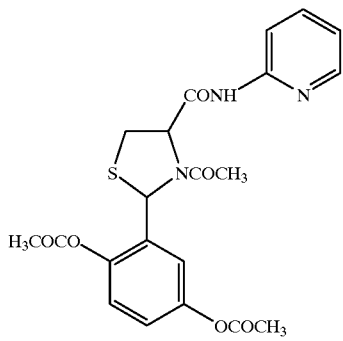

The procedure described above for preparation of 3-acetyl-2-(2,5-dihydroxyphenyl)-1,3-thiazolidine-N-(5-methyl-2-thiazolyl)-4-carboxamide (15) was followed for the preparation of 21, except that pyridine and a dimethyl ester of the thiazolidine starting material were employed.

EXAMPLE 22

Pharmacokinetic Studies of Vanillin-thiazolidine Adduct and Vanillin by Oral Administration in Rats Sixteen Sprague-Dawley rats (male, 200–300 g) were catheterized at the carotid at least 12 hours before drug administration and the catheter was flushed with heparin solution to prevent line clotting. The cannulated rats were then separated into two groups, one group (n=8) received an oral dose of 100 mg/kg vanillin and the other group (n=8) received 186 mg/kg (equivalent to 100 mg/kg of vanillin) of the vanillin-derived thiazolidine compound, both by oral gavage. Blood samples were collected by unhooking the flush syringe and letting the blood flow freely into centrifuge tubes at predetermined time points, i.e., 2, 5, 10, 15, 30, 45, 60, 90, 120 and 180 minutes after gavage. To each 100 μl of blood sample was added 400 μl of perchloric acid in a centrifuge tube. After vigorously vortexing, the samples in centrifuge tubes were spun down at 13,000 rpm for 10 min. The upper layer solution was transferred into autosampler vials and the vanillin contents were analyzed by HPLC using UV detection: Mobile phase solvents (v/v) consisted of 70% acetonitrile and 30% of acetic acid in water (1%). The elution profile showed a retention time of 6.5 min for vanillin.

The blood concentration of vanillin at each time point was calculated and utilized in a pharmacokinetic analysis. Mean vanillin pharmacokinetic parameters after oral administration of vanillin-thiazolidine adduct or vanillin in rats is shown in FIG. 1 herein. A striking difference was noted between the pharmacokinetic profiles of vanillin-thiazolidine and of unmodified vanillin. Whereas the vanillin levels in the blood of rats administered unmodified vanillin were low with a short half-life (closed rectangles), the vanillin levels in the blood of rats administered vanillin-derived thiazolidine were higher, with a much longer half-life (closed circles).

Noncompartmental pharmacokinetic analysis was then carried out using WinNolin (Pharsight Inc., Mountain View, Calif.) and the results are summarized in Table 1, below. By comparing the AUC (area under the curve) values, it is seen that the vanillin blood level in the vanillin-derived thiazolidine group was 37 times higher than that in the unmodified vanillin group. In addition, the half-life of vanillin in the blood of the vanillin-derived thiazolidine group was 4 times longer than that in the unmodified vanillin group. The maximum concentration at 2 minutes (Cmax) was also approximately 4 times higher in the former compared to the latter. These results are all consistent with the notion that the vanillin-derived thiazolidine compound greatly improves the bioavailability of vanillin compared to unmodified vanillin. This suggests that the vanillin-derived thiazolidine is an excellent protected form of vanillin for oral delivery of vanillin to treat sickle cell anemia patients.

TABLE 1

Mean vanillin pharmacokinetic parameters after oral administration of vanillin-thiazolidine adduct or vanillin in rats

| Drug | Tmax (min) | Cmax (at 2 min) | βt½ (min) | AUClast (ug*min/mL) | AUCinf | N |
|---|---|---|---|---|---|---|
| Vanillin-Thiazolidine Adduct (equivalent 100 mg/kg vanillin) | 8.4 ± 4.1 | 10.13 ± 7.59 | 45 ± 18 | 559 ± 449 | 610 ± 449 | 8 |
| Vanillin (100 mg/kg) mean pooled data | 5 | 2.45 ± 4.48 | 11 | 15 | 16 | 8 |

Tmax = the time to maximum concentration
Cmax = the maximum concentration at 2 minutes
βt½ = the terminal phase of half life
AUClast = the area under the curve from zero to the last time point
AUCinf = the area under the curve from zero to infinite time It is speculated that the mechanisms by which the vanillin-derived thiazolidine improves vanillin bioavailability are manifold. It is well known that vanillin can be extensively metabolized by intestinal bacteria and the liver (Strand and Scheline, supra). It is likely that the vanillin-derived thiazolidine is not easily metabolized by the same routes. Secondly, the vanillin-derived thiazolidine is more hydrophobic than vanillin, a property that may improve its intestinal absorption as well.

While the invention has been described in detail with reference to certain preferred embodiments thereof, it will be understood that modifications and variations are within the spirit and scope of that which is described and claimed.

What is claimed is:

1. A method for increasing in vivo stability of a therapeutic organic aldehyde, said method comprising incorporating said aldehyde into a protected organic aldehyde.

2. The method according to claim 1 wherein the protected organic aldehyde is an imine, a macrocyclic ester/imine, an acetal, an hemiacetal, a macrocyclic ester/hemiacetal, an alcohol, a macrocyclic diester, a cyclic acetal, or a thiazolidine.

3. The method according to claim 2 wherein the thiazolidine has the structure I:

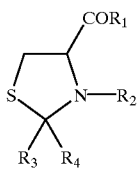

(I)

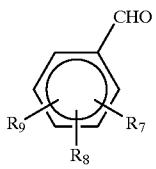

(II)

wherein $R_1$ is —OH, alkoxy, substituted alkoxy, cycloalkoxy, substituted cycloalkoxy, aryloxy, substituted aryloxy, heteroaryloxy, substituted heteroaryloxy, or $N(R_5)_2$ wherein each $R_5$ is independently H, alkyl, substituted alkyl, alkenyl, substituted alkenyl, aryl, substituted aryl, heteroaryl, or substituted heteroaryl, wherein $R_2$ is H or —X—$R_6$ wherein X is carbonyl or sulfonyl and $R_6$ is alkyl, substituted alkyl, aryl, substituted aryl, alkylaryl, or substituted alkylaryl, and wherein one of $R_3$ and $R_4$ is H and the other is H, alkyl, substituted alkyl, cycloalkyl, substituted cycloalkyl, alkenyl, substituted alkenyl, aryl, substituted aryl, heteroaryl, or substituted heteroaryl, and wherein $R_3$ and $R_4$ are derived from the aldehyde.

4. The method to claim 3 wherein $R_3$ and $R_4$ are derived from vanillin.

5. The method according to claim 3 wherein said vanillin is vanillin, o-vanillin, or isovanillin.

6. The method according to claim 3 wherein $R_3$ and $R_4$ are derived from 1-hexanal, hexen-2-al, heptanal, 1-octanal, 1-nonanal, decanal, tetradecanal, undecanal, undecenal, dodecanal, 2-methyl undecenal, hexyl cinnamaldehyde, amyl cinnamaldehyde, 3,4-dimethoxy benzaldehyde, dimethyl heptenal, 2-methyl-3-(p-isopropylphenol)-propionaldehyde, or 4-iso propyl benzaldehyde.

7. The method according to claim 3 wherein $R_3$ and $R_4$ are derived from an arylaldehyde.

8. The method according to claim 7 wherein the arylaldehyde has the structure II:

wherein each of $R_7$ $R_8$, and $R_9$ are optional and, if present, are independently —OH, alkyl, substituted alkyl, alkoxy, cycloalkoxy, acyloxy, cycloacyloxy, F, Cl, Br, $NO_2$, or cyano.

9. The method according to claim 8 wherein $R_7$ is ortho —OH.

10. The method according to claim 8 wherein $R_7$ is —OH and $R_8$ is —OH.

11. The method according to claim 10 wherein $R_7$ is ortho to said —CHO and $R_8$ is meta or para to said —CHO.

12. The method according to claim 8 wherein $R_7$ is —OH and R8 is —$OCH_3$.

13. The method according to claim 12 wherein $R_7$ is ortho to said —CHO and $R_8$ is meta or para to said —CHO.

14. The method according to claim 1 wherein the protected organic aldehyde provides a source of organic aldehyde that forms a Schiff base adduct with hemoglobin S in whole blood.

15. The method according to claim 1 wherein the protected organic aldehyde is administered in a pharmaceutically acceptable carrier.

16. The method according to claim 1 wherein the protected organic aldehyde is formulated for parental administration.

17. The method according to claim 1 wherein the protected organic aldehyde is formulated for oral administration.

18. The method according to claim 1 wherein a unit dose of the protected organic aldehyde is administered.

* * * * *

UNITED STATES PATENT AND TRADEMARK OFFICE
CERTIFICATE OF CORRECTION

PATENT NO. : 6,355,661 B1
DATED : March 12, 2002
INVENTOR(S) : Lai et al.

It is certified that error appears in the above-identified patent and that said Letters Patent is hereby corrected as shown below:

Column 26,
Line 34, change "parental" to -- parenteral --

Signed and Sealed this

Eleventh Day of February, 2003

JAMES E. ROGAN
*Director of the United States Patent and Trademark Office*